(12) United States Patent
Hill et al.

(10) Patent No.: US 12,004,725 B2
(45) Date of Patent: *Jun. 11, 2024

(54) INTRACORPOREAL TRANSILLUMINATION OF TISSUE USING LED ARRAY

(71) Applicant: Accendo Surgical, LLC, Tallahassee, FL (US)

(72) Inventors: David Allen Hill, Tallahassee, FL (US); Shawn Ramsey, Tallahassee, FL (US); William Roberts, Tallahassee, FL (US)

(73) Assignee: ACCENDO SURGICAL, LLC, Tallahassee, FL (US)

( * ) Notice: Subject to any disclaimer, the term of this patent is extended or adjusted under 35 U.S.C. 154(b) by 529 days.

This patent is subject to a terminal disclaimer.

(21) Appl. No.: 17/199,958

(22) Filed: Mar. 12, 2021

(65) Prior Publication Data
US 2021/0196112 A1 Jul. 1, 2021

Related U.S. Application Data

(63) Continuation of application No. 16/297,532, filed on Mar. 8, 2019, now Pat. No. 10,973,402, which is a (Continued)

(51) Int. Cl.
A61B 1/303 (2006.01)
A61B 17/42 (2006.01)
(Continued)

(52) U.S. Cl.
CPC .............. *A61B 1/303* (2013.01); *A61B 17/42* (2013.01); *A61B 90/30* (2016.02); *A61B 2017/00278* (2013.01); *A61B 2017/00283* (2013.01); *A61B 2017/00818* (2013.01); *A61B 17/1155* (2013.01); *A61B 2017/4216* (2013.01); *A61B 2090/309* (2016.02); *A61B 2090/3945* (2016.02); *A61B 2217/005* (2013.01); *A61B 2217/007* (2013.01)

(58) Field of Classification Search
CPC ......... A61B 1/303; A61B 90/30; A61B 17/42; A61B 1/3132
See application file for complete search history.

(56) References Cited

U.S. PATENT DOCUMENTS 8,603,105 B2 * 12/2013 Sauer ................. A61B 17/4241
606/119
8,663,239 B2 3/2014 Hess
(Continued)

*Primary Examiner* — Andrew Yang
(74) *Attorney, Agent, or Firm* — McDermott Will & Emery LLP; Judy M. Mohr

(57) ABSTRACT

A device which illuminates internal tissue and organs of a patient is described. The illumination member includes an array of light-emitting diodes ("LEDs"). The arrangement of the array depends on the configuration of the device and the procedure for which the device is being used. In all cases, the illumination member is used to illuminate relevant organs or structures in the body in order to increase visibility during surgical procedures. The LED array reduces the potential for inadvertent injury to internal structures for procedures located throughout the body. These procedures include those involving the reproductive organs of males and females, gastric and bariatrics, and other structures in the abdomen.

21 Claims, 13 Drawing Sheets

Related U.S. Application Data continuation of application No. 15/684,708, filed on Aug. 23, 2017, now Pat. No. 10,271,721, which is a continuation of application No. 14/295,550, filed on Jun. 4, 2014, now Pat. No. 9,743,955.

(60) Provisional application No. 61/830,696, filed on Jun. 4, 2013.

(51) Int. Cl.
*A61B 90/30* (2016.01)
*A61B 17/00* (2006.01)
*A61B 17/115* (2006.01)
*A61B 90/00* (2016.01)

(56) References Cited

U.S. PATENT DOCUMENTS

| | | |
|---|---|---|
| 9,743,955 B2 | 8/2017 | Hill et al. |
| 2015/0351621 A1 | 12/2015 | Hill et al. |
| 2017/0347870 A1 | 12/2017 | Hill et al. |

* cited by examiner

INTRACORPOREAL TRANSILLUMINATION OF TISSUE USING LED ARRAY

CROSS-REFERENCES TO RELATED APPLICATIONS

This application is a continuation of U.S. application Ser. No. 16/297,532, filed Mar. 8, 2019, now U.S. Pat. No. 10,973,402, which is a continuation of U.S. application Ser. No. 15/684,708, filed Aug. 23, 2017, now U.S. Pat. No. 10,271,721, which is a continuation of U.S. application Ser. No. 14/295,550, filed Jun. 4, 2014, now U.S. Pat. No. 9,743,955, which claims the benefit of U.S. Provisional Patent Application No. 61/830,696, filed Jun. 4, 2013, each of which is incorporated by reference herein in its entirety.

TECHNICAL FIELD

This invention relates to the field of devices fabricated for intracorporeal treatment of the human body. More specifically, the invention comprises a device which can illuminate certain tissue within a patient's body primarily by passing light through those tissues. The invention assists surgical operations in many ways, including clearly defining a location for an incision. The device, which can take many forms, uses embedded LED lights in order to illuminate the relevant tissue, organ or other structures.

BACKGROUND

The human body consists of a series of internal organs. Like the rest of the human body, internal organs are affected by disease, the inability to function properly, as well as other complications. In these instances, it may become important to investigate, or in the most extreme case, remove the problematic organ(s) or portions thereof. A doctor can investigate the state of a person's organs or tissue using endoscopy or laparoscopy. The term "endoscope" refers generally to a visualization tool—now typically a small digital camera—that may be inserted into a patient's body through an existing orifice or a small incision. Similar visualization devices have differing names depending upon their region of intended use. For example, a "laparoscope" is a visualization device that is intended for use in the patient's abdomen. Using an appropriate "scope" tissue that needs to be removed can be identified and excised using other surgical tools passed into the same area. Laparoscopy continues to become more popular as advancements are made in this field. If laparoscopy is an option for a patient's surgical procedure, then the benefits can be enormous compared to laparotomy. These advantages include reducing post-operative pain, shortening hospital stays, and reducing recovery times. Although laparoscopy is not always an option for surgery, these advantages have led to more surgical procedures that use laparoscopy or computer-aided laparoscopy.

In the case of laparoscopy and laparotomy, it is extremely important for the surgeon to have the clearest view possible. Of course, in the case of laparotomy this is less of a problem since the patient has a large incision that allows the surgeon to see into the patient's body using ambient light from the operating room and fixed lights shining onto the operation region. However, laparoscopic surgery is accomplished using only a few small incisions in the patient's body with all the structures having to be viewed through the small "scope."

Although laparoscopic surgery is less invasive than laparotomy, one commonly cited drawback is a lack of visibility of the operating area as it relates to visualizing hidden critical structures and the limited tactile feedback or the lack thereof altogether in robotic surgery applications. In laparoscopic surgery, this lack of visibility and tactile feedback can potentially lead to injury of vital structures including the ureters, bladder, major vessels, nerves as well as any other structures or organs in the relevant region of surgery (this depends on location of surgery). It would appear, then, that increased visibility would reduce the risk of injury during laparoscopic surgery.

One of many procedures that benefit from the use of laparoscopic surgery is a hysterectomy. A hysterectomy is the procedure in which a patient's uterus is surgically removed. There are several types of hysterectomies that can be performed. For example, a radical hysterectomy is the complete removal of the uterus, cervix, upper vagina, and parametrium. This type of hysterectomy is commonly used for the treatment of cancer. A total hysterectomy is the complete removal of the uterus and cervix, with or without oophorectomy (removal of the ovaries). A subtotal hysterectomy is the removal of the uterus, leaving the cervix in situ.

A common device used in laparoscopic hysterectomy is a uterine manipulator. A uterine manipulator is used to delineate the proper plane of dissection for colpotomy at the cervicovaginal junction (which is equipped with a colpotomy cup). In the event of a radical hysterectomy or a procedure involving a patient having cancer, a sponge stick is the preferred tool—due to the absence of a stem entering the uterus. While an intrauterine stem is helpful for retraction of the uterus, the risk of inadvertent uterine perforation transabdominally is increased, which can cause upstaging of the cancer due to cancer cells spilling into the abdomen. This must be avoided at all costs.

A hysterectomy is a procedure which is commonly performed using a laparoscopic or robotically assisted laparoscopic technique. Therefore, what is needed in this particular example is a device that increases the visibility of the location at which to cut and/or cauterize the tissue in order to remove the patient's uterus more safely and effectively. However, more generally, what is needed is a device that increases the visibility of the location within the body at which the surgical procedure is taking place. Oftentimes the objective is to cut or cauterize tissue, but the objective can include any number of procedures—such as drawing fluid, locating a structure, stapling tissue, or simply maneuvering an organ or other structure. The present invention achieves this objective, as well as others that are explained in the following description.

BRIEF SUMMARY OF THE INVENTION

The present invention comprises a device which illuminates internal tissue and organs of a patient. The device is available in many forms. The form of the device is dependent on the procedure for which the device is used. Each device includes an array of light-emitting diodes ("LEDs"). The arrangement of the array also depends on the configuration of the device and the procedure for which the device is being used. In the case of the example given in the preceding text, a hysterectomy, the LED array is positioned in the form of a ring embedded within a colpotomy cup. This allows the LED array to transilluminate the tissue surrounding the cervix (illuminate the critical area by actually passing light through a portion of the tissue). When performing a laparoscopic hysterectomy a surgeon inserts a laparoscope and a cutting or cauterization device through ports in a patient's abdomen. At the same time, a uterine manipulator is often passed through the vagina and into the uterus (often with a "cup" encircling the cervix). Thus, the tissue of the patient is being physically manipulated from one side of an enclosed volume (inside the vagina/uterus) while the actual incision is being performed on the opposite side of this volume (inside the abdomen but outside the uterus.

In the present invention, an array of powerful LED lights is provided on the end of a specially shaped distal end of an elongate member. As an example, in the case of a hysterectomy, the distal end may assume the form of a colpotomy ring with the LED array being disposed about the circumference of the ring. When the LED lights are illuminated the surgeon is able to easily and efficiently locate the colpotomy ring behind the relevant tissue by way of transillumination. The LED array is located inside the vagina/cervix and the surgeon can see the light from the LED's passing through the wall of the cervix. Thus, the LED array device allows the surgeon to make an incision at the proper location to best remove the uterus safely and effectively.

Although the example provided is that of a hysterectomy with an LED array in the shape of a ring, the LED array of the present invention may be applied to many procedures and devices. The LED array reduces the potential for inadvertent injury to internal structures for procedures located throughout the body. These procedures include those involving the reproductive organs of males and females, gastric and bariatrics, and other structures in the abdomen.

Figure 1:
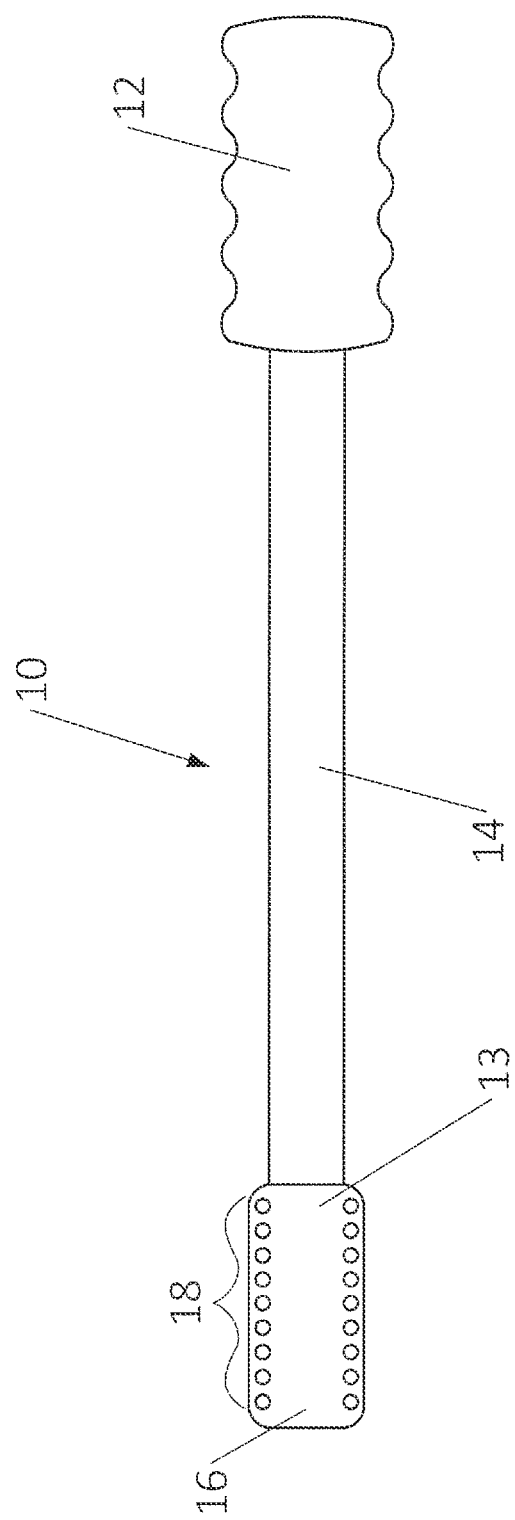
FIG. 1 is a perspective view, showing a preferred embodiment of the present invention for a generic surgical procedure.

| REFERENCE NUMERALS IN THE DRAWINGS | |
|---|---|
| 10 | illumination member |
| 12 | member handle |
| 13 | LED mounting surface |
| 14 | elongate member |
| 16 | distal end |
| 18 | LED array |
| 20 | uterine manipulator |
| 22 | colpotomy ring |
| 24 | intrauterine balloon |
| 26 | control handle |
| 28 | elongate member |
| 30 | positioning member |
| 32 | cutting device |
| 34 | vaginal canal |
| 36 | cervix |
| 38 | body of patient |
| 40 | tissue |
| 42 | LED |
| 44 | LED power cord |
| 46 | balloon |
| 48 | LED adjustment knob |
| 50 | uterus |
| 52 | suction port |
| 53 | irrigation port |
| 54 | esophagus |
| 56 | stomach |
| 58 | antrum |
| 59 | suction port |
| 60 | bladder |
| 62 | penis |
| 64 | urethra |

DETAILED DESCRIPTION OF THE INVENTION

The present invention provides a device which illuminates a region of interest within a patient's body during surgery or other medical procedures. FIG. 1 shows a relatively simple embodiment that includes the preferred features. Illumination member 10 varies with each application for various procedures. Here, illumination member 10 includes member handle 12, LED mounting surface 13, elongate member 14, distal end 16, and light emitting diode ("LED") array 18.

In general, distal end 16 is inserted into the patient's body. Elongate member 14 creates distance between the operator and the cavity in which illumination member 10 is inserted. Although elongate member 14 is shown as a cylinder with a linear axis in space, it may have a curved axis in space. It may also include features allowing it to be bent in various ways to conform to the relevant anatomy. In addition, LED array 18 is shown as two linear arrays, but LED array 18 can take many forms such as a curved array, a circular array, or any other planar shape including a singular LED. Most of these embodiments will be demonstrated in the following examples of alternate embodiments of the present invention.

Figure 2:
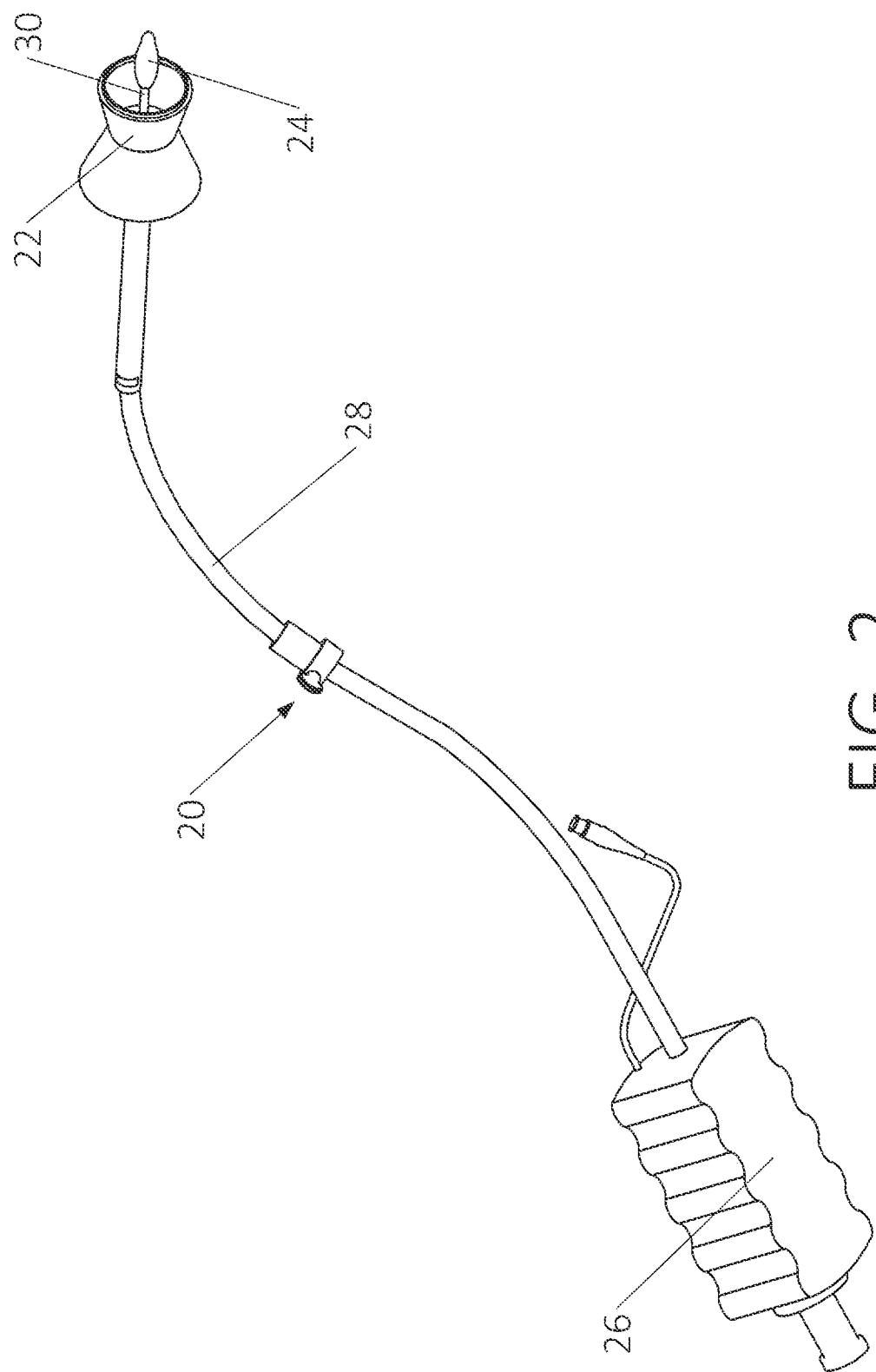
FIG. 2 is a perspective view, showing a prior art uterine manipulator.

One of the primary applications for illumination member 10 is that of a hysterectomy, or the removal of a uterus and/or other reproductive organs. In order to aid the reader's understanding, it is helpful to consider some prior art instruments used in this procedure. FIG. 2 illustrates a prior art uterine manipulator 20 in conjunction with a colpotomy ring 22 and an intrauterine balloon 24. This type of prior art device is typically used in a laparoscopic hysterectomy. As illustrated, uterine manipulator 20 includes a control handle 26 and elongate member 28, which attaches to colpotomy ring 22, positioning member 30 and pneumo-occluder balloon 24. In use, the colpotomy ring 22 is inserted into the vaginal canal of the patient until the colpotomy ring 22 reaches the vaginal fornices and cervix. The intra-uterine balloon 24 is directed into the uterus of the patient and is expanded inside of the uterus in order to secure the device. A series of ports are inserted through the abdomen of the patient which allows accommodation of the laparoscope and other suture or specialized laparoscopic instruments such as cutting/cauterizing devices, specimen retrieval bag, Endo Stitch suture-assist device or a tissue morcellator.

Figure 3:
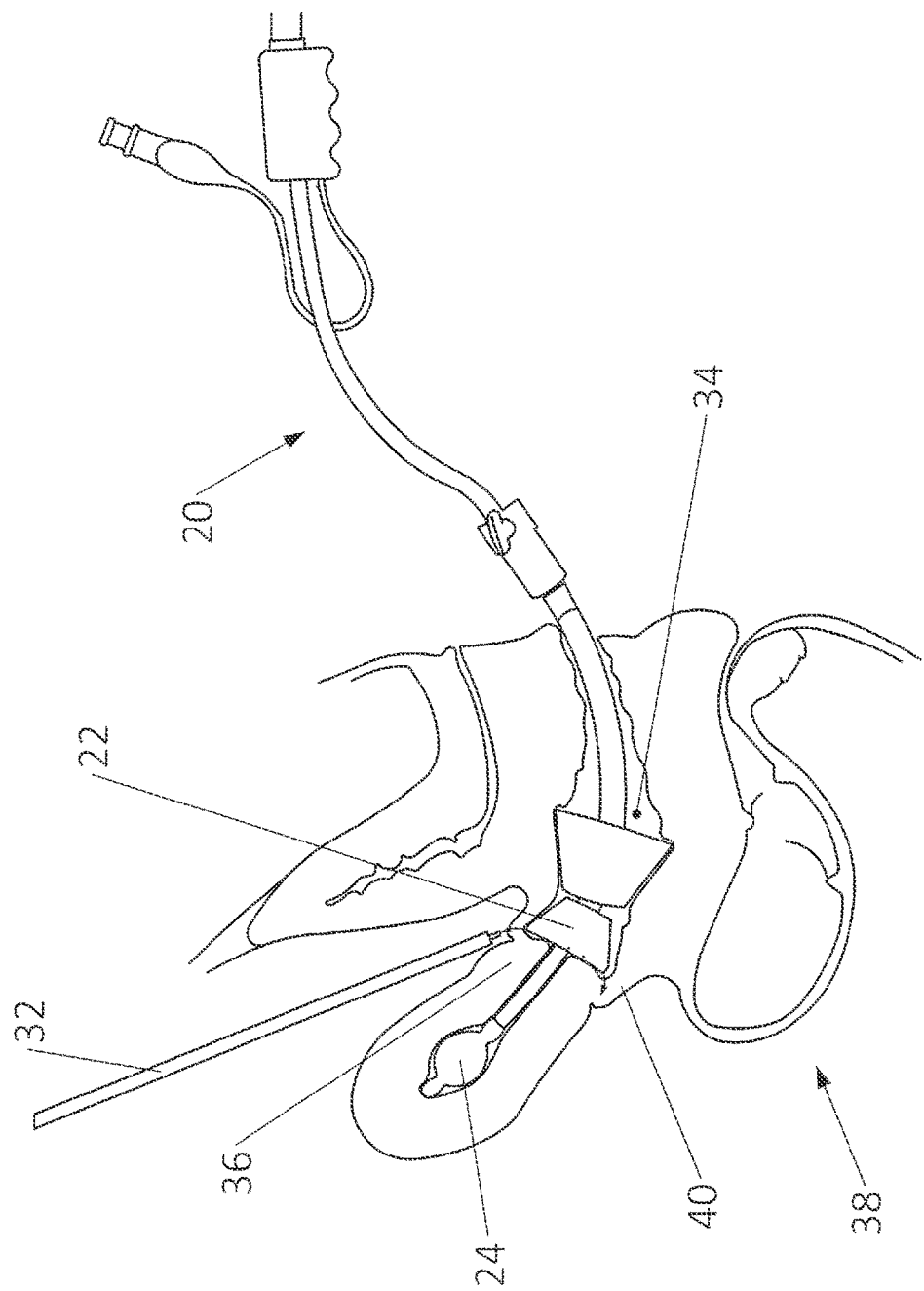
FIG. 3 is a schematic view, showing a prior art device in use.

The reader will appreciate that a variety of laparoscope instruments can be used to perform a hysterectomy. Thus, the application should not be limited by the use of any specific instruments. As illustrated in FIG. 3, the cutting device 32 enters the patient's body such that the relevant tissue to be cut or cauterized is between the cutting device 32 and the colpotomy ring 22. The viewing device is typically inserted next to cutting device 32. Thus, the viewing device cannot directly see the location of the colpotomy ring other than by noting the bulge it creates in the cervical tissue. The surgeon may therefore have a difficult time identifying the exact location at which the tissue should be cut or cauterized.

As illustrated, uterine manipulator 20 is fully inserted into the vaginal canal 34. Intrauterine balloon 24 is inflated in order to keep uterine manipulator 20 in position. Colpotomy ring 22 is positioned within the vaginal fornices at the opening of the cervix 36. During the operation a cutting device 32 enters the patient's body 38 through a port (not shown). The surgeon must position cutting device 32 such that as the cut through the tissue 40 is made, the cuff of the colpotomy ring 22 is on the opposing side.

Figure 4:
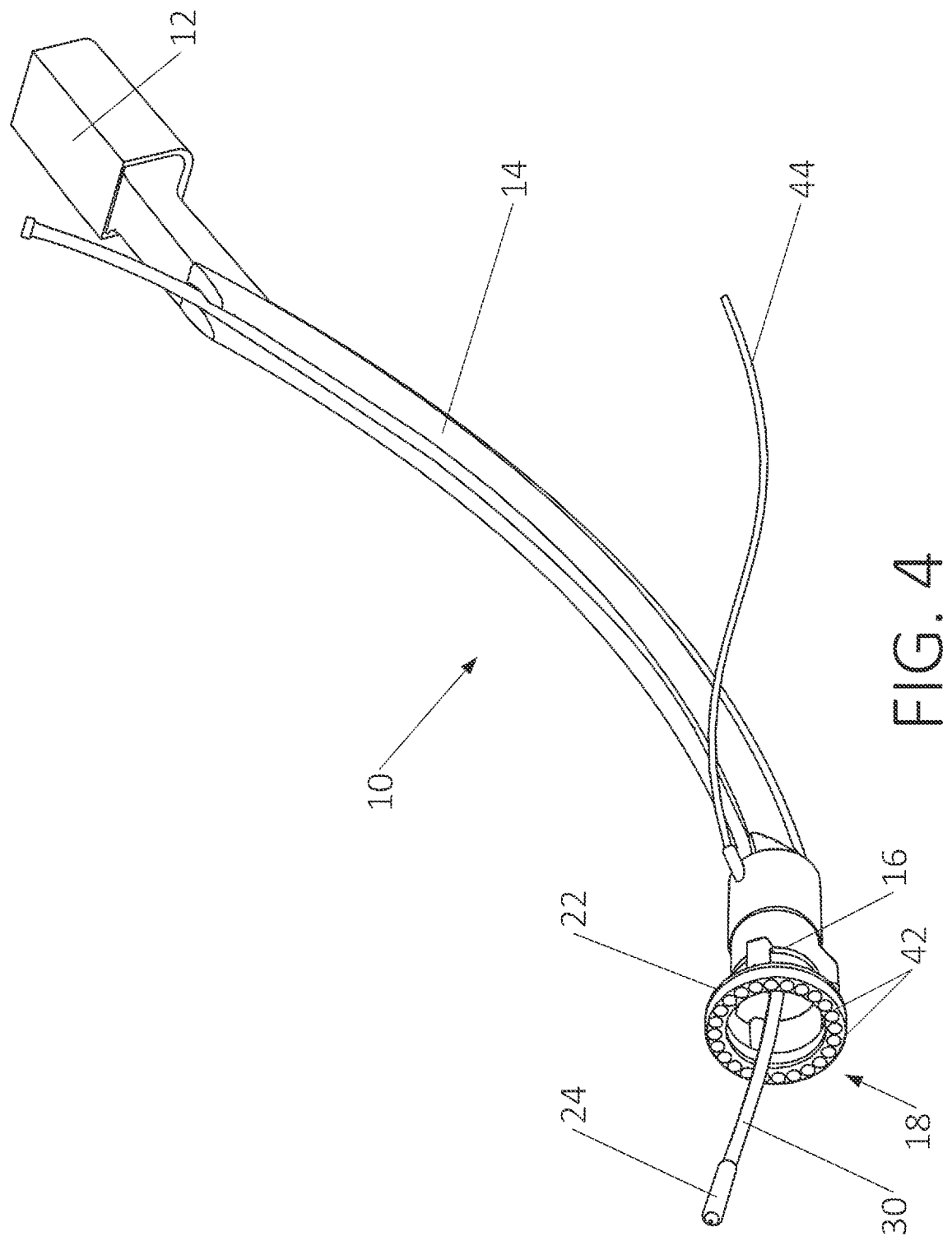
FIG. 4 is a perspective view, showing a preferred embodiment of the present invention.

FIG. 4 shows an embodiment of the present invention used for this same hysterectomy procedure. Illumination member 10 replaces uterine manipulator 20 and its associated colpotomy ring. In a preferred embodiment, illumination member 10 includes member handle 12, elongate member 14, distal end 16, and LED array 18 (as discussed in the preceding text). In addition to the primary elements, this embodiment of illumination member 10 includes colpotomy ring 22, intrauterine balloon 24, and positioning member 30. The reader will note that an important difference between prior art uterine manipulator 20 and this embodiment of illumination member 10 is the addition of LED array 18. Also, illumination member 10 preferably includes LED power cord 44 (which may run internally within elongate member 14). Preferably, LED power cord 44 leads to a power switch device (not shown). In a preferred embodiment, the switch has multiple functions, including the capability of switching the LEDs ON/OFF, dimming and brightening, flashing, etc.

Figure 5:
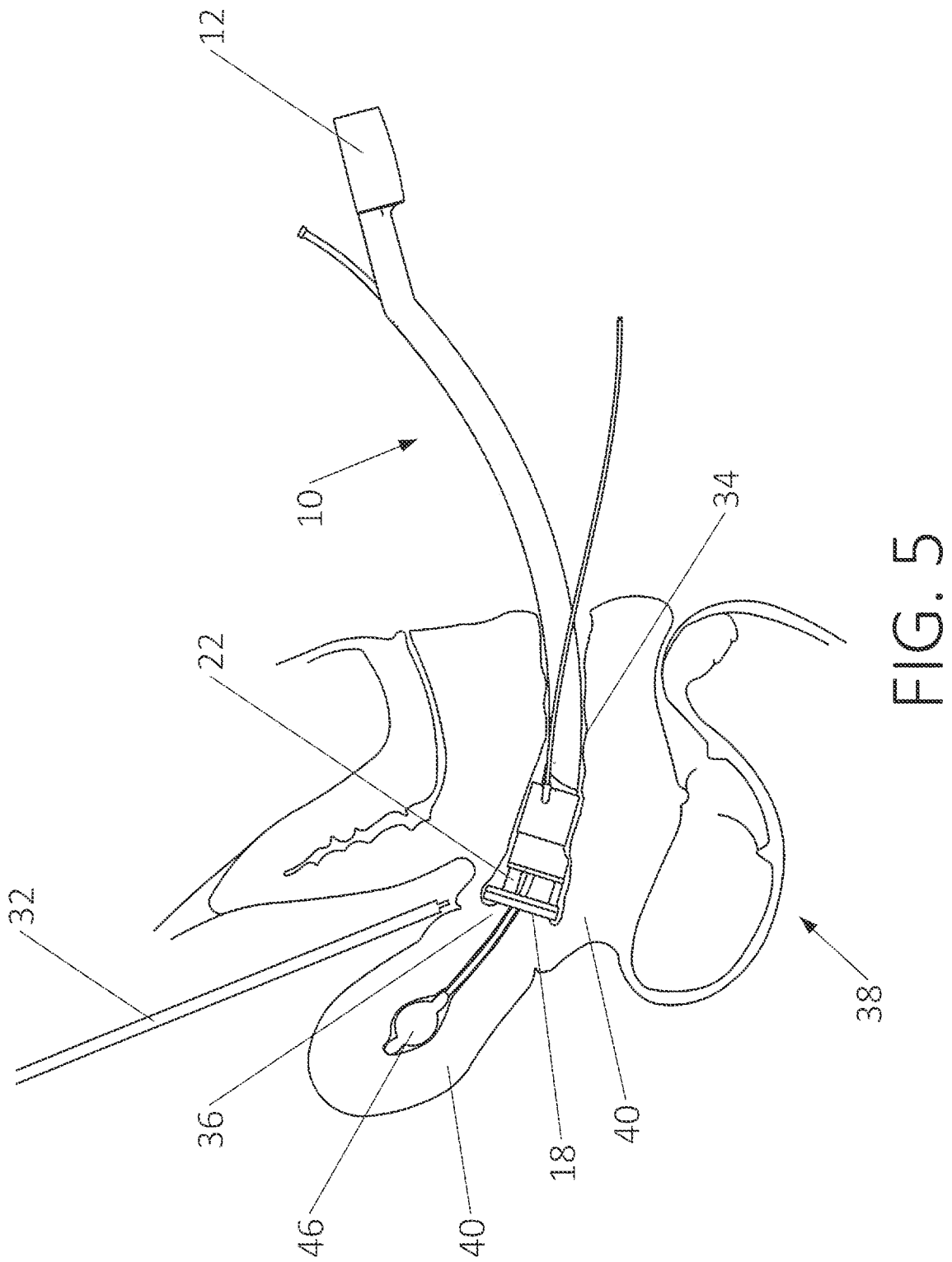
FIG. 5 is a schematic view, showing the embodiment of FIG. 4 in use during a hysterectomy procedure.

FIG. 5 illustrates the embodiment of FIG. 4 being used in a laparoscopic surgery. As illustrated, illumination member 10 is fully inserted into the vaginal canal 34. Colpotomy ring 22 is positioned within the vaginal fornices at the opening of the cervix 36. LED array 18 is located at the upper cuff of the colpotomy ring 22. During the operation a cutting device 32 enters the patient's body 38 through a port (not shown). The surgeon must position cutting device 32 such that as the cut through the tissue 40 is made, the cuff of the colpotomy ring 22 is on the opposing side.

The present illumination member 10 allows the surgeon to effectively see through the tissue to identify the exact location of colpotomy ring 22. When the LED's are switched on, they shine through the tissue wall defining the cervix. The surgeon, who is looking through the laparoscope on the opposite side of the tissue wall, can actually see the LED's and thereby precisely visualize the location of the colpotomy ring. As discussed above, LED lights 42 can be brightened if tissue 40 is thick and difficult to see through or can be selectively dimmed as the tissue is cut so that the light is not too bright.

This procedure illustrates a general case of the invention's use. It is most effective in illuminating a tissue wall that separates a first volume within a patient's body from a second volume. In the case of laparoscopic surgery of FIG. 5, the first volume is contained within the vagina/cervix/uterus. Access to this volume is obtained through a first opening in the patient's body (the vagina). Illumination member 10 is inserted through the vagina and thereby gains access to this first volume.

The second volume in this scenario is the volume within the abdominal cavity that lies outside the vagina/cervix/uterus. Access to this second volume is obtained via an incision. The LED array is then placed against the tissue wall and the LED's are illuminated. The light from the LED's shines through the tissue wall and becomes visible in the second volume.

Illumination of the relevant tissue in the first volume of the patient allows the surgeon to identify the location of that tissue via laparoscope inserted into the second volume of the patient. In the case of a hysterectomy, that tissue is to be cut in order to remove the patient's uterus. However, other surgical action can be taken. Surgical action can take many forms—some examples include cutting, grasping, cauterizing, scraping, stitching, puncturing, securing, strengthening, viewing, reshaping, stapling, or removing. The reader will note that this is not meant to be an exhaustive list of all the surgical actions that can be accomplished, but rather some examples given to demonstrate the large number of surgical actions. Thus, the scope of the present invention should not be limited to any single surgical action.

The reader will also note that tissue 40 creates a wall of tissue between the first and second volumes as described in the preceding text. In the case of the hysterectomy, that wall of tissue is the region where surgical action is required. Transillumination of the wall of tissue indicates to the surgeon which region to cut. In general, a wall of tissue may separate the first volume and the second volume. It should be noted, however, that surgical action does not necessarily occur at the wall of tissue. In fact, the wall of tissue may simply provide the barrier between the two volumes.

Figure 6:
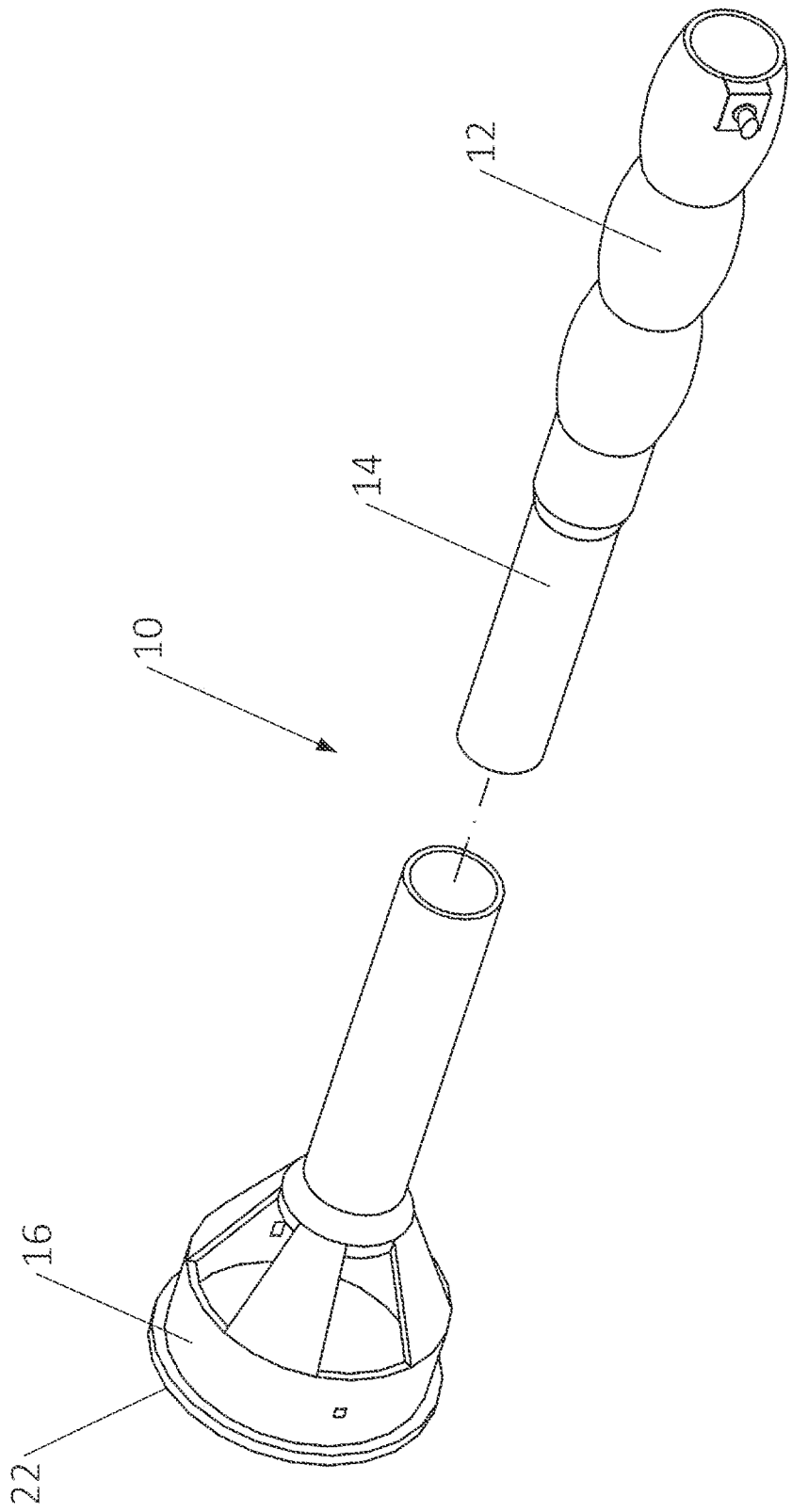
FIG. 6 is a perspective view, showing an alternate embodiment of the present invention.

Oftentimes, especially in the case of cancer, it is dangerous to insert positioning member 30 and intra-uterine balloon 46 into the uterus. In the case of accidental perforation of the uterus, cancerous cells could spill into the abdomen. Typically, a doctor will use ring forceps grasping a sponge instead of uterine manipulator 20 in order to avoid entering the uterus. This technique allows for very limited manipulation of the tissue while limiting the risk of uterine perforation by entering the uterus. FIG. 6 shows an alternate embodiment of illumination member 10 that is intended to deal with this situation. The reader will notice that the embodiment illustrated is similar to uterine manipulator 20. Illumination member 10 includes member handle 12 and colpotomy ring 22 located on distal end 16. This particular embodiment of illumination member 10 allows the surgeon to transilluminate the relevant tissue surrounding the cervix (as discussed in the preceding text) without any pieces entering the uterus. Thus, even in the case of cancer in the uterus or other complications, LED array 18 can be utilized in order to more readily and effectively perform a hysterectomy.

Figure 7:
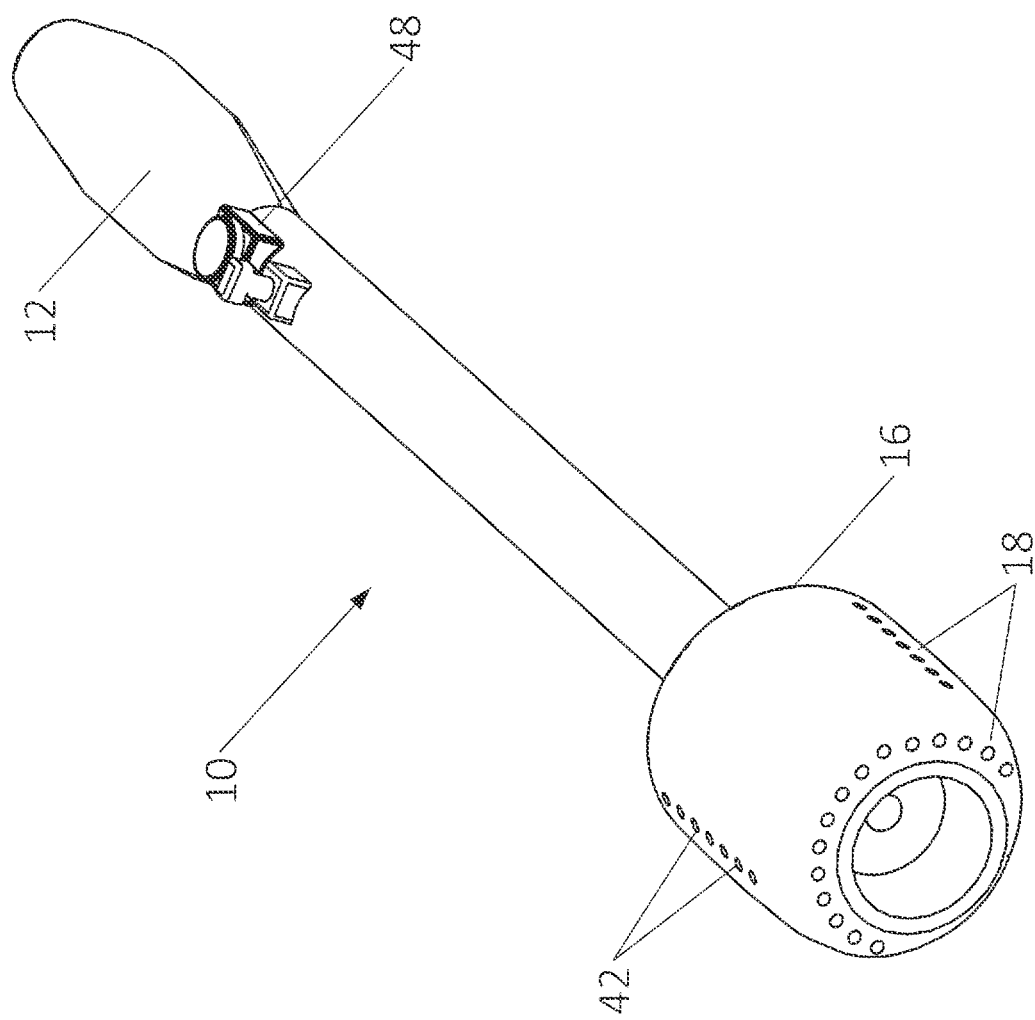
FIG. 7 is a perspective view, showing another alternate embodiment of the present invention.

Still another embodiment of the illumination member 10 is shown in FIG. 7. The reader will note that the distal end 16 of illumination member 10 is enlarged compared to the previous embodiment. As illustrated, LED array 18 can take the form of a ring or LEDs 42 can span distal end 16 axially. The organization of LEDs 42 on distal end 16 is dependent on the application of illumination member 10. Thus, the reader should not limit the scope of the present invention based on the form or placement of LED array 18.

Figure 8:
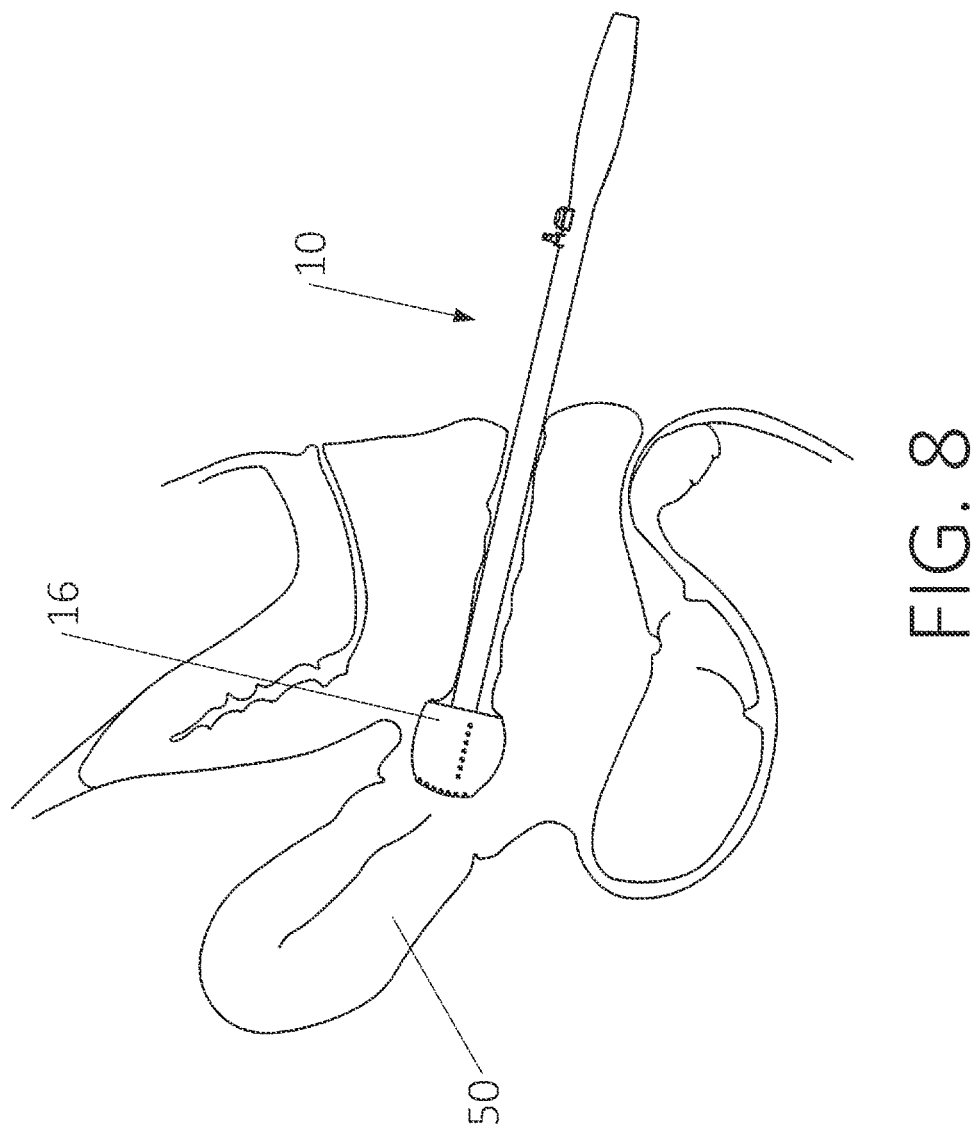
FIG. 8 is a schematic view, showing the embodiment of FIG. 7 in use.

The embodiment of illumination member 10 in FIG. 7 is used as a vaginal plane delineation device. The device is used as a transvaginal retraction and positioning device for vaginal vault dissection during a sacrocolpopexy surgical procedure. FIG. 8 shows the device in use. LED array 18 allows for transillumination of the vaginal vault in order to better delineate the vesicovaginal plane and the rectovaginal plane.

Figure 9:
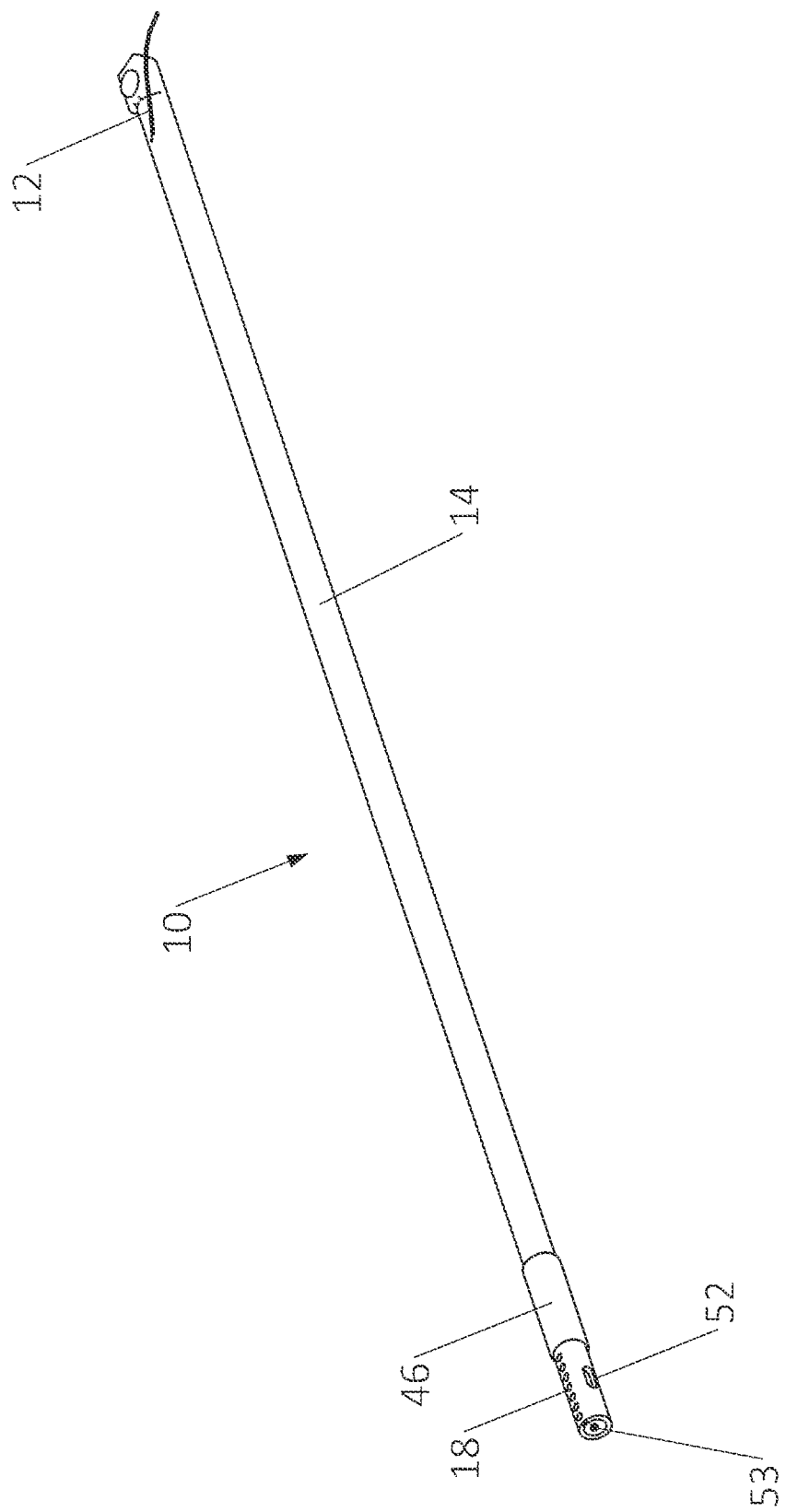
FIG. 9 is a perspective view, showing another alternate embodiment of the present invention.
Figure 10:
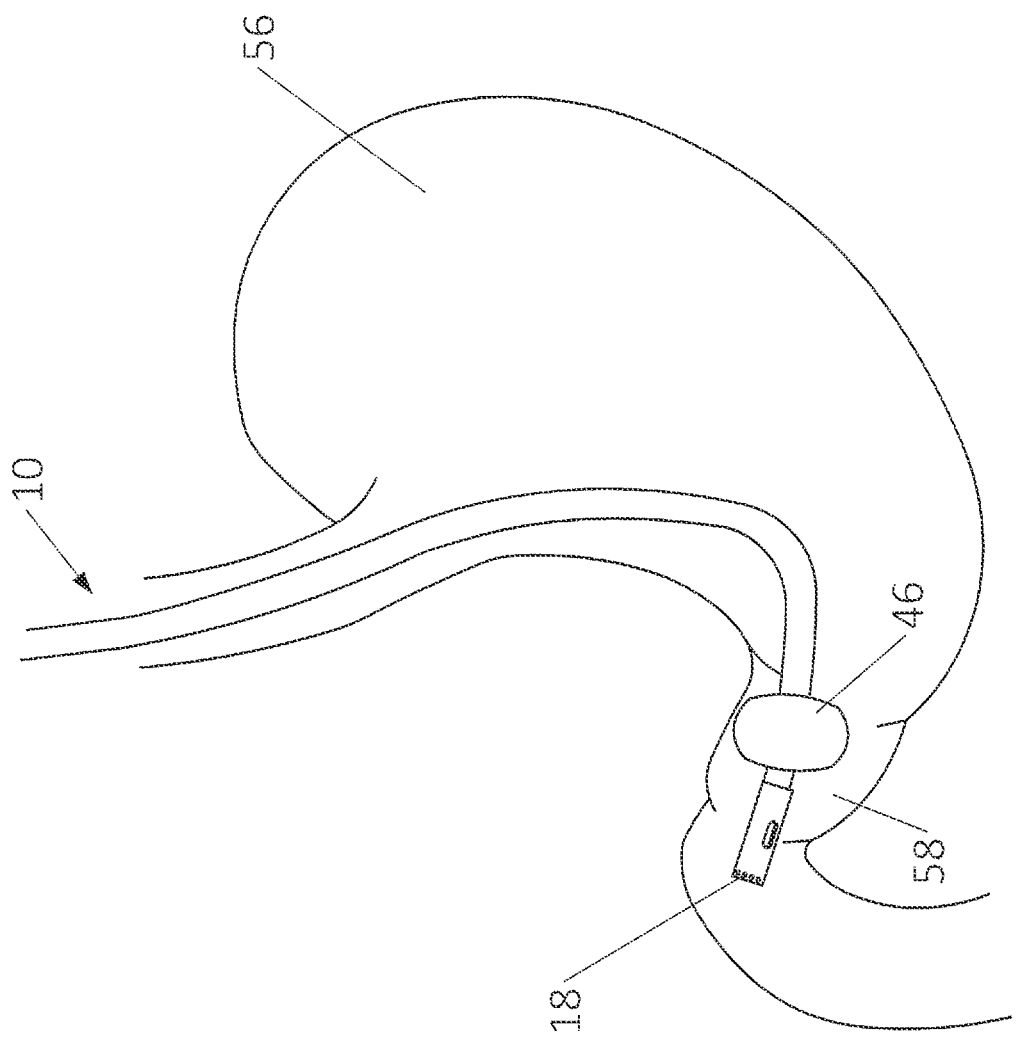
FIG. 10 is a schematic view showing the embodiment of FIG. 9 in use.

FIG. 9 shows yet another alternate embodiment of illumination member 10. FIG. 10 illustrates the application of this particular embodiment. Preferably, the embodiment of illumination member 10 in FIG. 9 is used in gastric and bariatric surgical procedures in order to provide visible and tactile delineation of the antrum of the stomach. Illumination of this region using LED array 18 allows a surgeon to easily identify the placement of the distal end 16 of the device 10. In addition, illumination member 10 preferably includes components similar to those of a gastric calibration tube such as suction port 52. In addition, illumination member preferably includes irrigation port 53. Suction port 52 and irrigation port 53 allow the surgeon to add and remove liquid during a procedure in the gastric channel.

This particular embodiment of the present invention is inserted into the patient's esophagus 54, through stomach 56 and into antrum 58. The reader will note that this particular embodiment is preferably made flexible in order to navigate the gastric channel. It may also include guiding wires that a surgeon can employ to manipulate the curvature and deflection direction of the device. In a preferred embodiment, elongate member 14 is fabricated from a soft, hollow conduit such as silicone. LED array 18 is preferably located at the very tip of distal end 16. Preferably, member handle 12 includes a check valve mated with a syringe (not shown) which is used to fill balloon 46.

Figure 11:
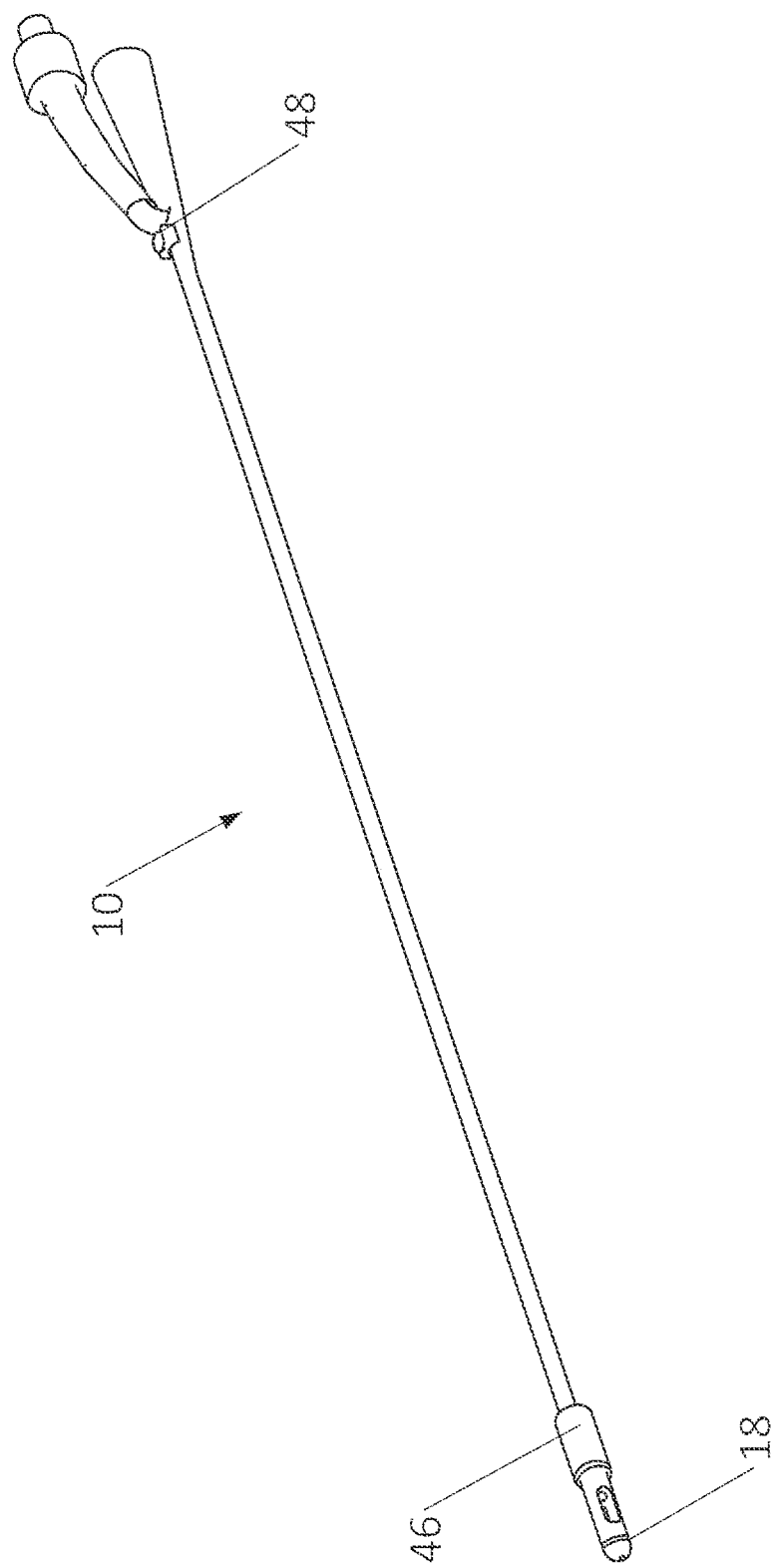
FIG. 11 is a perspective view, showing yet another alternate embodiment of the present invention.
Figure 12:
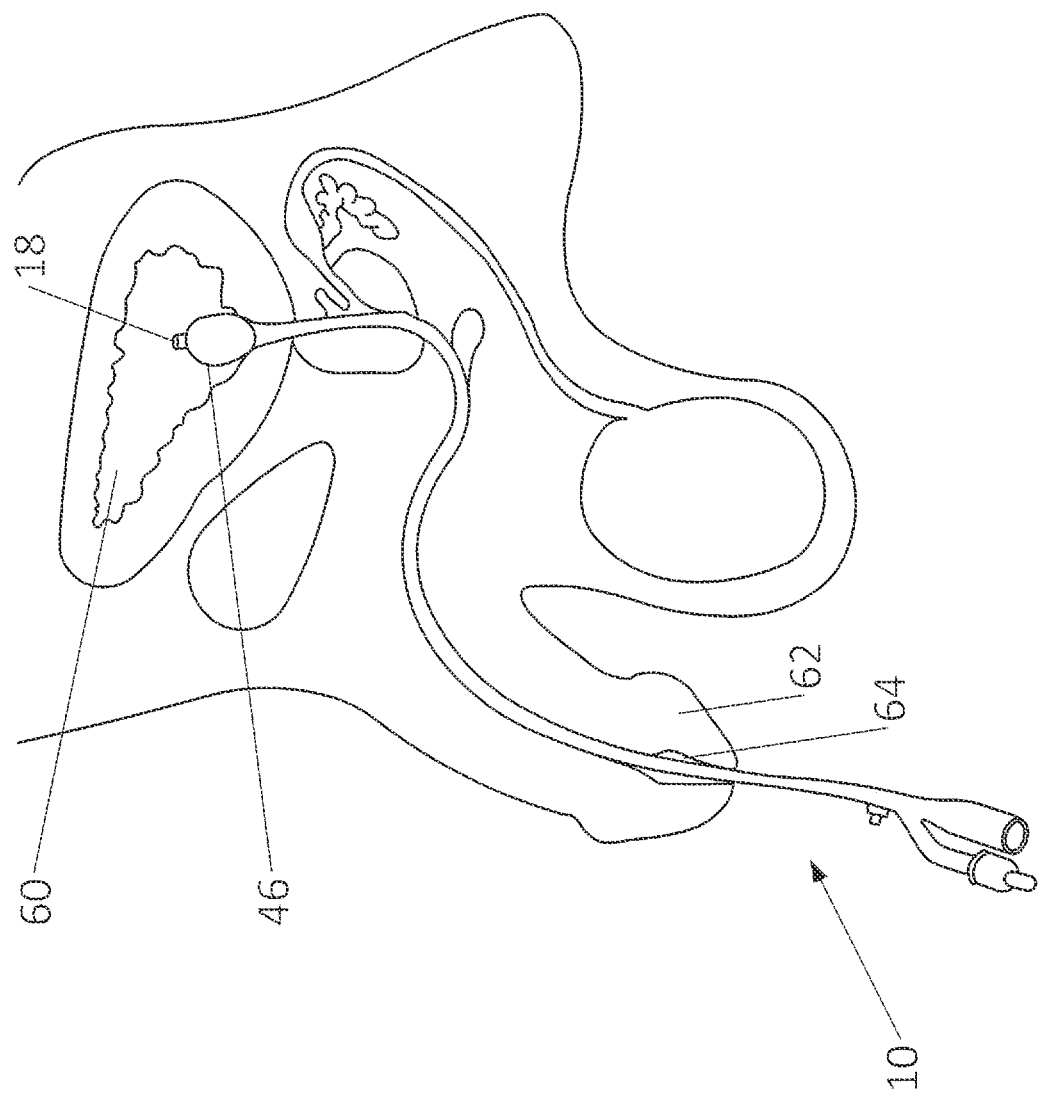
FIG. 12 is a schematic view, showing the embodiment of FIG. 11 in use.

FIGS. 11 and 12 illustrate the application of illumination member 10 as a Foley catheter. This embodiment includes the all of the components of a typical prior art Foley catheter with the addition of LED array 18. In addition to the management of urination, a catheter is also used to identify the bladder during surgical procedures. Preferably, elongate member 14 is fabricated from a flexible, hollow material. The preferred embodiment of the present invention includes two hollow conduits—one is used for the drainage of urine and the other is to inflate balloon 46. LED array is preferably embedded into balloon 46, but can also be attached at the tip of distal end 16 as illustrated.

As illustrated, illumination member 10 is inserted into the urethra 64, spanning the length of penis 62 and into bladder 60. By illuminating LED array 18 within bladder 60, surgeons working in the abdominal cavity proximate the bladder can positively identify the location of the bladder, thereby avoiding accidental injury to the bladder and surrounding structures.

Figure 13:
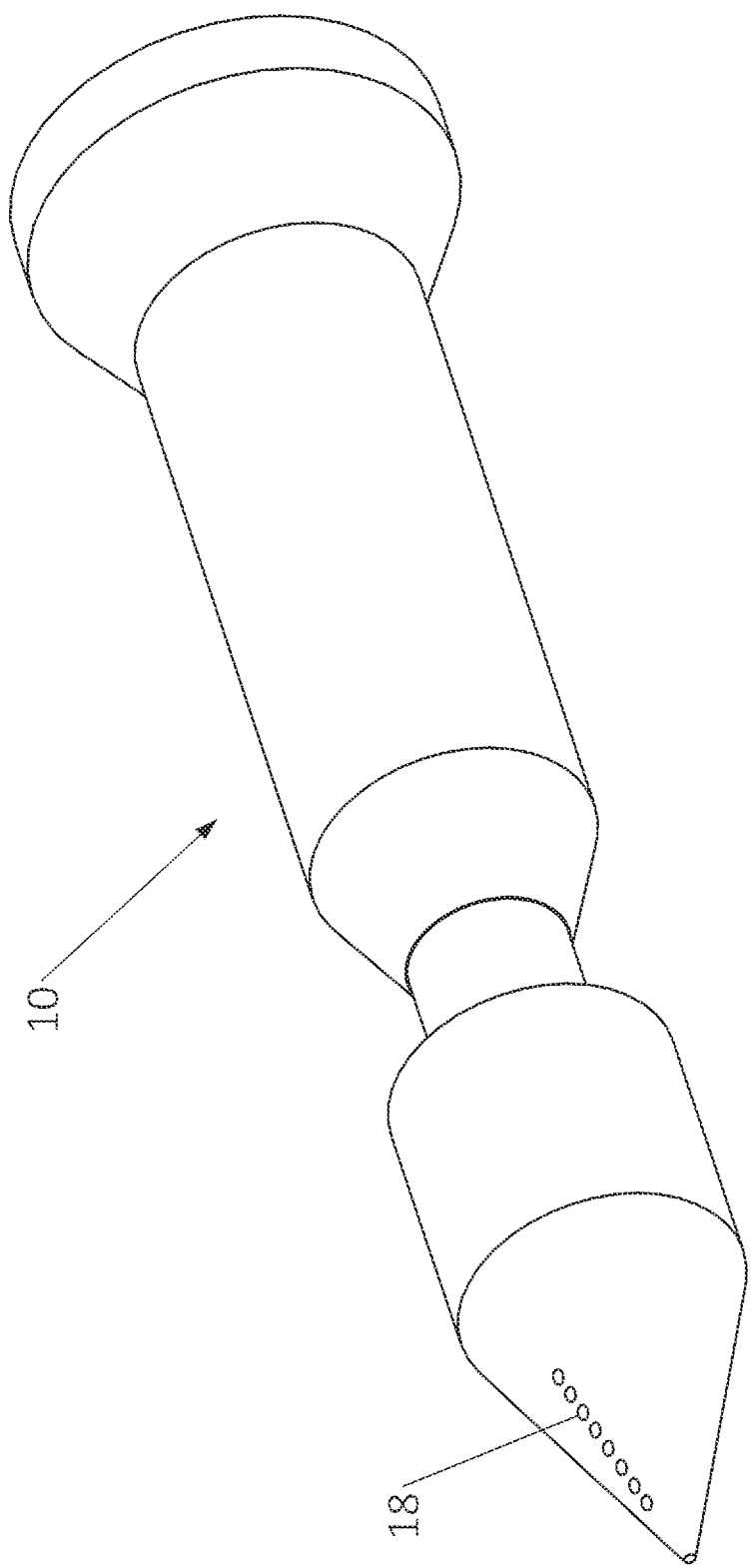
FIG. 13 is perspective view, showing an alternate embodiment of the present invention.

A circular stapler spike is used to perform anastomoses in a patient. The spike portion is coupled with an anvil in the alimentary canal for the creation of end-to-end, end-to-side, and side-to-side anastomoses. FIG. 13 shows illumination member 10 in the form of the spike used for anastomoses. LED array 18 allows illumination of the region of interest inside the patient during a surgical procedure. Preferably, illumination member 10 is a disposable spike which replaces the original spike on a circular stapler device. However, illumination member 10 can also take the form of a sheath that fits over the original spike on the stapler device. In either form, the spike increase visibility for the surgeon in order to perform anastomoses.

Returning to the embodiment of FIG. 7, some preferred features of the invention will be discussed in more detail. The reader will note that the distal end of the illumination member assumes the form of a shaped surface (in this case a cylinder with a smoothly filleted leading edge). It is preferable to contour this surface so that it rests smoothly against the anatomy it is intended to contact. The portion of this surface that contains the LED array is known as an "array mounting surface." This surface is shown generally in FIG. 1, but it is preferably included with each embodiment. This surface is preferably shaped to place the LED's in position against the relevant tissue wall. Of course, in some cases a simple shape will suffice.

Each embodiment of the present invention preferably includes a power source and controller for the LED array. Preferably, the power source is a lithium-ion rechargeable battery. However, in the case where the illumination member is disposable, along with the circuitry, a less expensive power supply can be used—such as AA batteries. The controller for the LED array can be as simple as a power ON/OFF switch. In the preferred embodiment of illumination member, the LED controller has dimming functionality. In some embodiments, the LED power source and controller are integral to the member handle. This is the preferred configuration, but may not be possible in all embodiments.

LED lights are particularly beneficial when applied to devices that enter the body or contact the tissue of a patient and in use during a laparoscopic surgery because of the natural properties of a LED light, namely, that LED lights are small in area and can achieve high brightness while remaining cool to the touch. Further, LED lights are powerful, have lower energy consumption and have a longer lifetime. Thus, it is important that the present ring device include light-emitting diodes lights.

The preceding description contains significant detail regarding novel aspects of the present invention. It should not be construed, however, as limiting the scope of the invention but rather as providing illustrations of the preferred embodiments of the invention. Thus, the scope of the invention should be fixed by the following claims, rather than by examples given.

It is claimed:

1. A device for in vivo transillumination of a tissue, comprising:
    a flexible elongate member comprising a channel formed between a proximal end and a distal end;
    a handle attached to the proximal end;
    a mounting surface immovably secured to the distal end of the elongate member, the mounting surface comprising an array of light emitting diodes (LEDs) configured for visualizing the LEDs for locating the mounting surface on one side of an in vivo tissue wall that separates a first volume within a human body from a second volume by inspection from an opposing side of the in vivo tissue wall, wherein the mounting surface on one side of the first side of the tissue wall is visible on the opposing side of the tissue wall;
    an LED power cord coupled to the distal end of the elongate member for supplying power from a power source to the array of LEDs; and
    a controller coupled to the LED power cord for controlling power to one or more LEDs in the array of LEDs.

2. The device of claim 1, wherein the array of LEDS is embedded in the mounting surface.

3. The device of claim 1, wherein the mounting surface is secured on the distal end of the elongate member.

4. The device of claim 1, wherein the elongate member is a cylinder having a smooth outer surface.

5. The device of claim 1, wherein the mounting surface is selected from a cylindrical shaped surface, a spherical shaped surface, and a planar shaped surface.

6. The device of claim 1, wherein the power source is a battery.

7. The device of claim 1, wherein the controller is an on/off switch.

8. The device of claim 1, wherein the controller has a variable illumination intensity adjustment feature, a variable illumination color adjustment feature, or a variable illumination pulsing feature.

9. The device of claim 1, wherein the elongate member comprises two hollow conduits.

10. The device of claim 1, wherein the elongate member is disposable.

11. The device of claim 1, wherein the device is disposable.

12. The device of claim 1, further comprising a positioning member arranged in the channel of the elongate member and extending through the distal end of the elongate member.

13. A method for in vivo transillumination of a tissue, comprising:
providing a device of claim 1,
whereby when the device is inserted into a first volume of a human body separated from a second volume by a tissue wall having a first side and an opposing side, the mounting surface on one side of the first side of the tissue wall is visible on the opposing side of the tissue wall.

14. The method of claim 13, whereby said mounting surface contacts the tissue wall on the first side when the device is inserted into the first volume of a human body.

15. The method of claim 13, wherein said first volume comprises a patient's uterus and said second volume comprises a patient's abdomen.

16. The method of claim 13, wherein the tissue separating the first volume and the second volume is the cervicovaginal junction.

17. The method of claim 16, wherein the mounting surface is a cylindrical surface.

18. The method of claim 13, wherein the first volume includes a patient's vaginal canal and the second volume includes a patient's abdomen.

19. The method of claim 18, wherein the tissue separating the first volume and the second volume is a vaginal wall.

20. The method of claim 19, wherein the mounting surface is a cylindrical or annular surface.

21. The method of claim 13, wherein the first volume includes a patient's gastrointestinal tract and the second volume includes a patient's abdomen.

* * * * *